(12) United States Patent
Nakayama et al.

(10) Patent No.: US 10,272,517 B2
(45) Date of Patent: Apr. 30, 2019

(54) BONDING STATE INSPECTION METHOD

(71) Applicant: Nissan Motor Co., Ltd., Yokohama-shi, Kanagawa (JP)

(72) Inventors: Hirotaka Nakayama, Kanagawa (JP); Taewon Kim, Kanagawa (JP); Yukinari Goto, Kanagawa (JP); Toru Sato, Kanagawa (JP); Takashi Matsuoka, Kanagawa (JP)

(73) Assignee: Nissan Motor Co., Ltd., Yokohama (JP)

( * ) Notice: Subject to any disclaimer, the term of this patent is extended or adjusted under 35 U.S.C. 154(b) by 126 days.

(21) Appl. No.: 15/305,120

(22) PCT Filed: Apr. 7, 2015

(86) PCT No.: PCT/JP2015/060887
§ 371 (c)(1),
(2) Date: Oct. 19, 2016

(87) PCT Pub. No.: WO2015/190165
PCT Pub. Date: Dec. 17, 2015

(65) Prior Publication Data
US 2018/0178313 A1 Jun. 28, 2018

(30) Foreign Application Priority Data

Jun. 12, 2014 (JP) .................... 2014-121697

(51) Int. Cl.
*B23K 20/10* (2006.01)
*G01N 29/04* (2006.01)
(Continued)

(52) U.S. Cl.
CPC .............. *B23K 20/10* (2013.01); *B23K 20/26* (2013.01); *B23K 31/12* (2013.01); *B23K 31/125* (2013.01);
(Continued)

(58) Field of Classification Search
CPC .............. B29C 65/08; B29C 66/92443; B29C 66/66915; B23K 20/10; B23K 31/125
See application file for complete search history.

(56) References Cited

U.S. PATENT DOCUMENTS

| 4,040,885 A | * | 8/1977 | Hight ..................... B23K 20/10 156/378 |
| 5,431,324 A | | 7/1995 | Kajiwara et al. |

(Continued)

FOREIGN PATENT DOCUMENTS

| DE | 3429776 A1 | 2/1986 | |
| DE | 4321874 A1 | * 1/1995 | ............. B23K 20/10 |

(Continued)

*Primary Examiner* — John Fitzgerald
(74) *Attorney, Agent, or Firm* — Global IP Counselors, LLP

(57) ABSTRACT

Provided is a bonding state inspection method to accurately determine the quality of the bonding state of plate materials that have been ultrasonically bonded. The bonding state inspection method comprises a measuring step in which the rate of energy transfer rate to an anvil is measured each time a vibrating horn is pressed against a plurality of superimposed, plate materials on the anvil and the plate materials are ultrasonically bonded; a calculation step in which a variable threshold is calculated using the energy transfer rate measured each time of the ultrasonic bonding; and a determination step in which the quality of the bonding state of the plate materials is determined based on comparison between the magnitude of the energy transfer rate measured in the measuring step and the variable threshold calculated in the calculation step of the previous ultrasonic bonding.

15 Claims, 11 Drawing Sheets

(51) Int. Cl.
  *B23K 31/12* (2006.01)
  *B23K 20/26* (2006.01)
(52) U.S. Cl.
  CPC .......... *G01N 29/04* (2013.01); *G01N 29/045* (2013.01); *G01N 2291/0231* (2013.01)

(56) References Cited

U.S. PATENT DOCUMENTS

| | | | |
|---|---|---|---|
| 5,523,956 A | 6/1996 | Cawelti et al. | |
| 5,658,408 A * | 8/1997 | Frantz | B29C 66/92921 156/359 |
| 5,732,873 A | 3/1998 | Topping et al. | |
| 5,855,706 A * | 1/1999 | Grewell | B06B 1/023 156/358 |
| 6,827,247 B1 * | 12/2004 | Fan | B23K 20/10 228/1.1 |
| 8,020,746 B2 * | 9/2011 | Geissler | B23K 20/005 156/580.1 |
| 8,021,504 B2 * | 9/2011 | Gabler | B23K 20/10 156/64 |
| 2006/0225842 A1 * | 10/2006 | Darcy, III | B29C 65/08 156/580.1 |
| 2009/0314412 A1 * | 12/2009 | Gabler | B23K 20/10 156/64 |
| 2011/0308736 A1 * | 12/2011 | Scheuerman | B23K 20/106 156/378 |
| 2013/0199296 A1 * | 8/2013 | D'Angelo | B23K 26/032 73/588 |

FOREIGN PATENT DOCUMENTS

| | | | |
|---|---|---|---|
| DE | 4429684 A1 * | 2/1996 | ............ B23K 20/10 |
| EP | 567426 A2 * | 10/1993 | |
| JP | 5-115986 A | 5/1993 | |
| JP | 2005-271028 A | 10/2005 | |
| JP | 2005-271029 A | 10/2005 | |
| JP | 2010-503536 A | 2/2010 | |
| WO | 2008/031823 A1 | 3/2008 | |

\* cited by examiner

BONDING STATE INSPECTION METHOD

CROSS-REFERENCE TO RELATED APPLICATIONS

This application is a U.S. National stage application of International Application No. PCT/JP2015/060887, filed Apr. 7, 2015, which claims priority to Japanese Patent Application No. 2014-121697 filed in Japan on Jun. 12, 2014.

BACKGROUND

Field of the Invention

The present invention relates to a bonding state inspection method.

Background Information

In the ultrasonic bonding or welding, for example, two metal plates are placed in a state of being superimposed or stacked on an anvil, a vibrating horn is pressed to join or bond the two metal plates for solid-phase bonding.

In this connection, in Japanese Laid Open Patent Application No. H5-115986 A identified below, a monitoring method has been proposed for determining the quality of ultrasonic bonding, in which, by measuring the vibration of the anvil during ultrasonic bonding, the measured waveform of vibration is compared to a standard waveform. According to the monitoring method disclosed in Japanese Laid Open Patent Application No. H5-115986 A, the quality of the bonding state of two metal plates that have been ultrasonically bonded can be easily determined.

SUMMARY

However, in the above monitoring method, since the measured waveform of vibration of the anvil is to be compared with a standard waveform, when the measured waveform of vibration is different from the standard waveform, the bonded state is determined to be defective. Incidentally, in the ultrasonic bonding, the measured waveform of vibration of the anvil may change over time depending on the course of the lifetime of a tool to be used in the ultrasonic bonding. For example, the anvil is worn by use, and the vibration amplitude of the anvil worn tends to decay over time in accordance with the bonding number of ultrasonic bonding. Therefore, even a product the bonding state of which would be determined to be acceptable by performing a tensile test is determined to be defective when the measured waveform is different from the standard waveform and is determined defective due to the monitoring method described above. Thus, a problem of poor accuracy arises.

The present invention has been made to solve the problem described above, and an object thereof is to provide a bonding state inspection method for determining the quality of the bonding state of the ultrasonic bonded plate-shaped members accurately.

In a bonding state inspection method according to the present invention, for achieving the above object, a measuring step, a calculation step, and a determination step are provided. In the measuring step, each time a vibrating horn is pressed against a plurality of superimposed plate materials placed on an anvil and ultrasonic bonding is performed, an energy transfer rate to the anvil is measured. In the calculation step, by using the energy transfer rate which is measured each time the ultrasonic bonding is performed, a variable threshold is calculated. Finally, in the determination step, by comparing the energy transfer rate which is measured in the measuring step with the magnitude of the variable threshold which has been calculated in the calculation step of the previous ultrasonic bonding, the quality of the bonding state of the plate materials will be determined.

In the bonding state inspection method according to the present invention, by comparing the energy transfer rate to the anvil to be measured each time the ultrasonic bonding is performed with the magnitude of the variable threshold calculated in the previous ultrasonic bonding, acceptability of the bonding state of the plate-like members is determined. Thus, even when the measured waveform of the vibration amplitude of the anvil is different from the standard waveform, a correct determination can be made. That is, it is possible to determine with accuracy the quality of the bonding state of the plate-like member.

BRIEF DESCRIPTION OF THE DRAWINGS

Referring now to the attached drawings which form a part of this original disclosure.

DETAILED DESCRIPTION OF THE EMBODIMENTS

Figure 1:
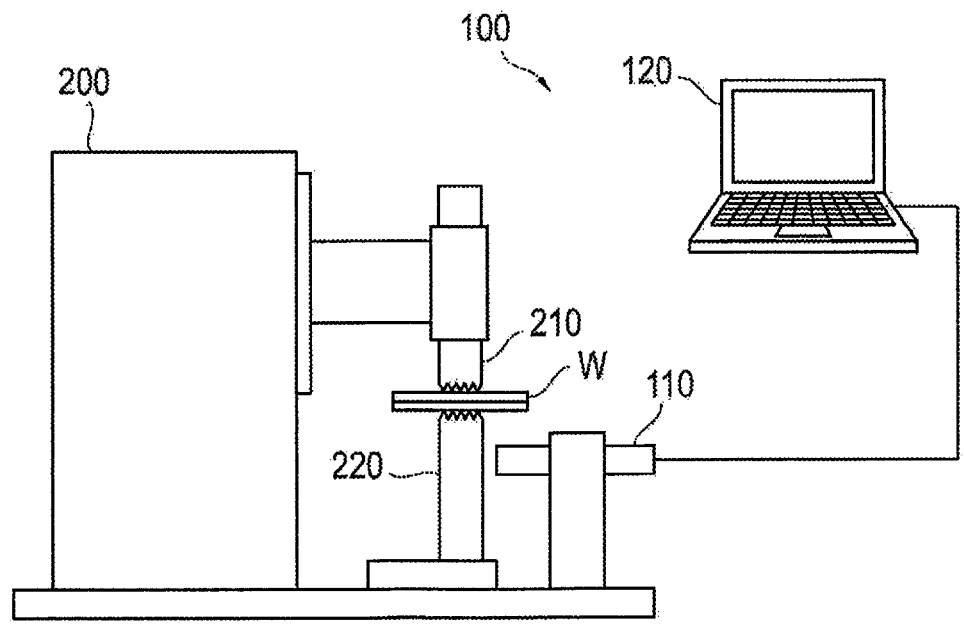
FIG. 1 is a diagram showing a schematic configuration of an inspection apparatus for applying the bonding state inspection method in a first embodiment.

Below, with reference to the accompanying drawings, a bonding state inspection method according to the present invention is detailed in a first embodiment and a second embodiment individually. Note that the same reference numerals are given to the same elements in the description of the drawings, without giving duplicate description thereof.

First Embodiment

Inspection Apparatus Applying a Bonding State Inspection Method

FIG. 1 is a diagram showing a schematic configuration of an inspection apparatus 100 to which the bonding state inspection method in the first embodiment is applied.

An inspection apparatus 100 inspects the bonding state of the plate material W to be ultrasonically bonded by an ultrasonic bonding apparatus 200. The ultrasonic bonding apparatus 200 includes a horn 210 to impart vibrations while pressing the sheet material W, and an anvil 220 on which the sheet material W is placed. At the tip of the horn 210 and the tip of the anvil 220 which is disposed opposite on the ultrasonic bonding apparatus 200, a plurality of protrusions having a pyramid shape are formed in a grid pattern.

The inspection apparatus 100, as shown in FIG. 1, includes a vibration sensor 110 for measuring the vibration amplitude of the anvil 220 of the ultrasonic bonding apparatus 200, and an analysis device 120 that determines the quality of the bonding state of the sheet material W on the basis of a signal from the vibration sensor 110.

The vibration sensor 110 is arranged on the side surface of the anvil 220 to measure the vibration amplitude of the anvil 220 during ultrasonic bonding. The vibration sensor 110 is connected to the analysis device 120 via the A/D converter (not shown). As the vibration sensor 110, a non-contact type displacement sensor such as an eddy current sensor or a laser-doppler displacement meter may be employed.

The analysis device 120 determines the quality of the bonding state of the sheet material W to be ultrasonically bonded. The analysis device 120 further analyzes the vibration waveform data obtained from the vibration sensor 110 by measuring the vibration amplitude of the anvil 220 and thus measures the energy transfer rate to the anvil 220. The analysis device 120 also uses the energy transfer rate which is measured each time of the ultrasonic bonding to calculate a variable threshold. The analysis device 120 further determines the acceptability of the bonding state of the two sheet materials W by comparing the measured energy transfer rate and the magnitude of the calculated variable threshold in the previous ultrasonic bonding. The analysis device 120 is, for example, a general personal computer.

Figure 2:
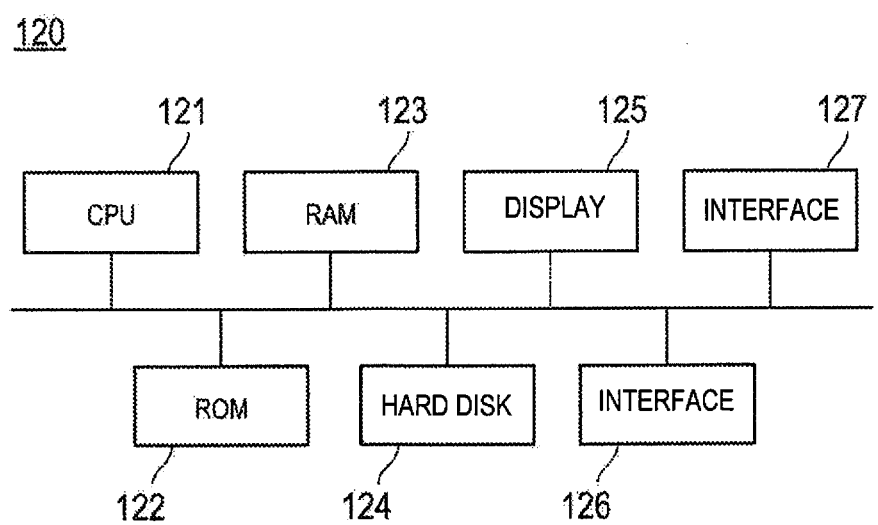
FIG. 2 is a block diagram showing a schematic configuration of an inspection apparatus shown in FIG. 1.

FIG. 2 is a block diagram showing a schematic configuration of the analysis device 120. The analysis device 120 includes a CPU 121, a ROM 122, a RAM 123, a hard disk 124, a display 125, an input unit 126 and an interface 127. These units are connected to each other via a bus.

The CPU 121 controls each of the units described above and performs various kinds of arithmetic processing according to a program. The ROM 122 stores various programs and various data in advance. The RAM 123 temporarily stores programs and data as a working area.

The hard disk 124 stores various programs and various data including an OS (operating system). In the hard disk 124, a program for inspecting the bonding state is stored.

The display 125 is, for example, a liquid crystal display, and displays of various kinds of information. The input unit 126 is, for example, a keyboard, a touch panel, or a pointing device such as a mouse used for inputting various information.

The interface 127 electrically connects the analysis device 120 and the vibration sensor 110. The interface 127 receives signals from the vibration sensor 110.

Incidentally, the analysis device 120 may contain constitutional elements other than those described above, or may lack a portion of the constitutional elements described above.

The inspection or test as constructed above determines the acceptability of the bonding state of the sheet materials W by comparing the energy transmission rate measured each time of the ultrasonic bonding of the sheet materials W by the ultrasonic bonding apparatus 200 and the magnitude of the variable threshold calculated in the previous ultrasonic bonding.

Inspection Method of Bonding State

Figure 3:
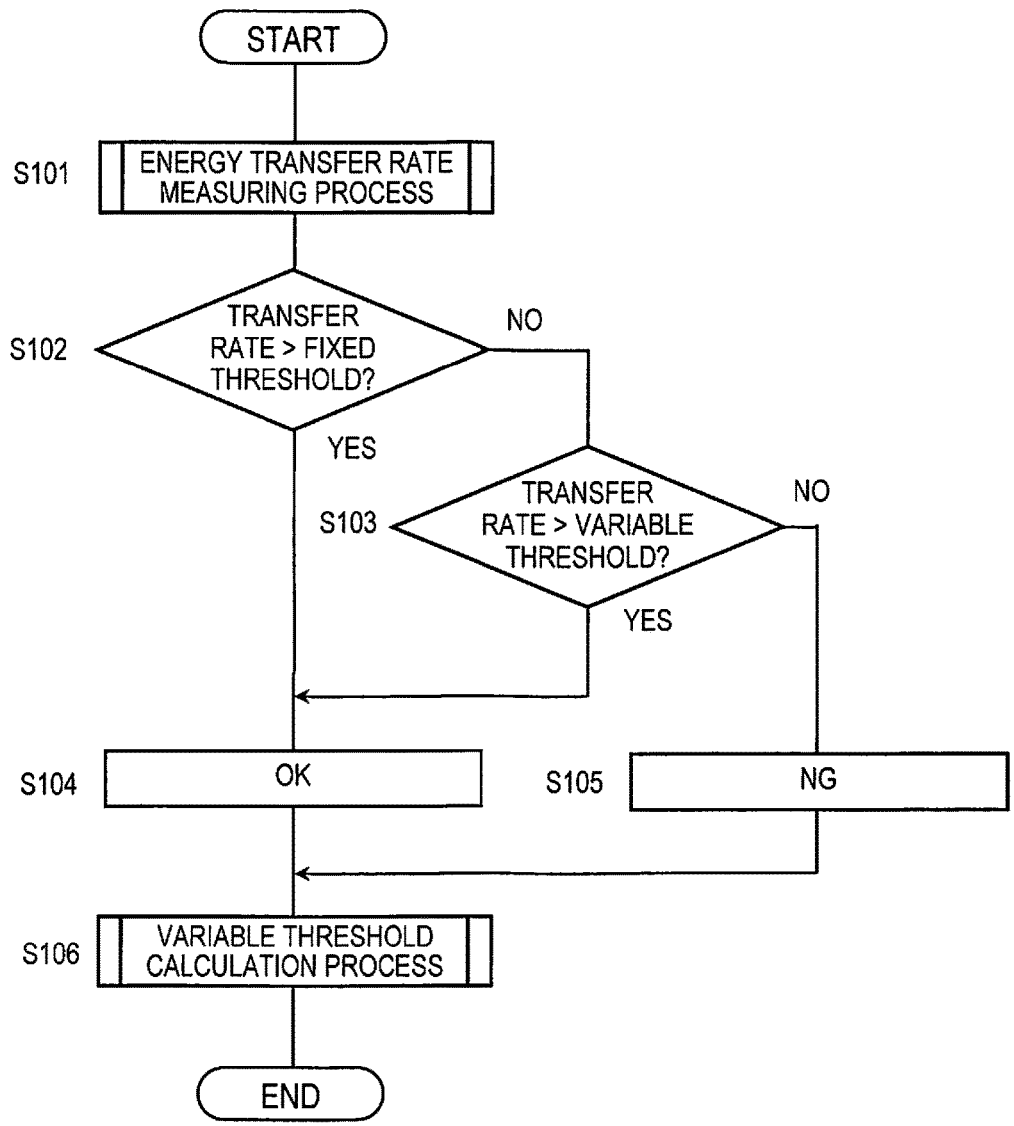
FIG. 3 is a flowchart showing a bonding state inspection process in the first embodiment.

Below, a description will be given of an inspection or testing method of the bonding state pertaining to a first embodiment. FIG. 3 is a flowchart showing a process of the bonding state inspection routine performed by the analysis device 120, which is executed each time the ultrasonic bonding is performed. Note that the algorithm shown in the flowchart of FIG. 3 is stored as a program in the hard disk 124 of the analysis device 120 and executed by the CPU 121.

First, an energy transfer rate measuring process is executed (step S101). Specifically, by analyzing by the analysis device 120 the vibration waveform data of the anvil 220 that is measured by the vibration sensor 110, the energy transfer rate to the anvil 220 (hereinafter, also referred to as "transmission rate") is calculated. Details about the energy transfer rate measuring process will be described below.

Subsequently, a determination is made whether or not the energy transfer rate calculated in the process shown in step S101 exceeds a fixed threshold (step S102). Here, the fixed threshold represents, for example, a value determined in advance statistically by taking the data for the transfer rate regarding a plurality sets of sheet materials which show a good bonding state determined by a tension test. The fixed threshold is previously stored in the hard disk 124 for each of tools used in the ultrasonic bonding and the materials and shapes of the sheet materials to be ultrasonically bonded.

When the transfer rate does not exceed the fixed threshold (in step S102: NO), a determination is made as to whether or not the transfer rate exceeds the variable threshold (step S103). Here, the variable threshold is calculated in the previous ultrasonic bonding, which is a value that varies over time depending on the bonding number of ultrasonic bonding. Note that the initial value of the variable threshold may have the same value as the fixed threshold.

When the transfer rate exceeds the fixed threshold (in step S102: YES), or when transfer rate exceeds the variable threshold without exceeding the fixed threshold (in step S102: NO and in step S103: YES), a determination is made that the bonding state is good (step S104).

On the other hand, when the transmission rate does not exceed the fixed threshold or the variable threshold (in step S102: NO and in step S103: NO), the bonding state is determined to be not good and unacceptable (step S105).

Subsequently, a variable threshold calculation process is executed (step S106). Specifically, each time the ultrasonic bonding is performed, by using the measured transfer rate in the process shown in step S101, a variable threshold is calculated. The calculation of the variable threshold is detailed below. The calculated variable threshold will be used to determine the quality of the subsequent bonding state of the ultrasonic bonding using the same anvil 220.

As described above, the analysis device 120 determines the quality of the bonding state of the plate material W each time ultrasonic bonding is performed by executing the process shown in the flowchart of FIG. 3.

Energy Transfer Rate Measuring Process

Figure 4:
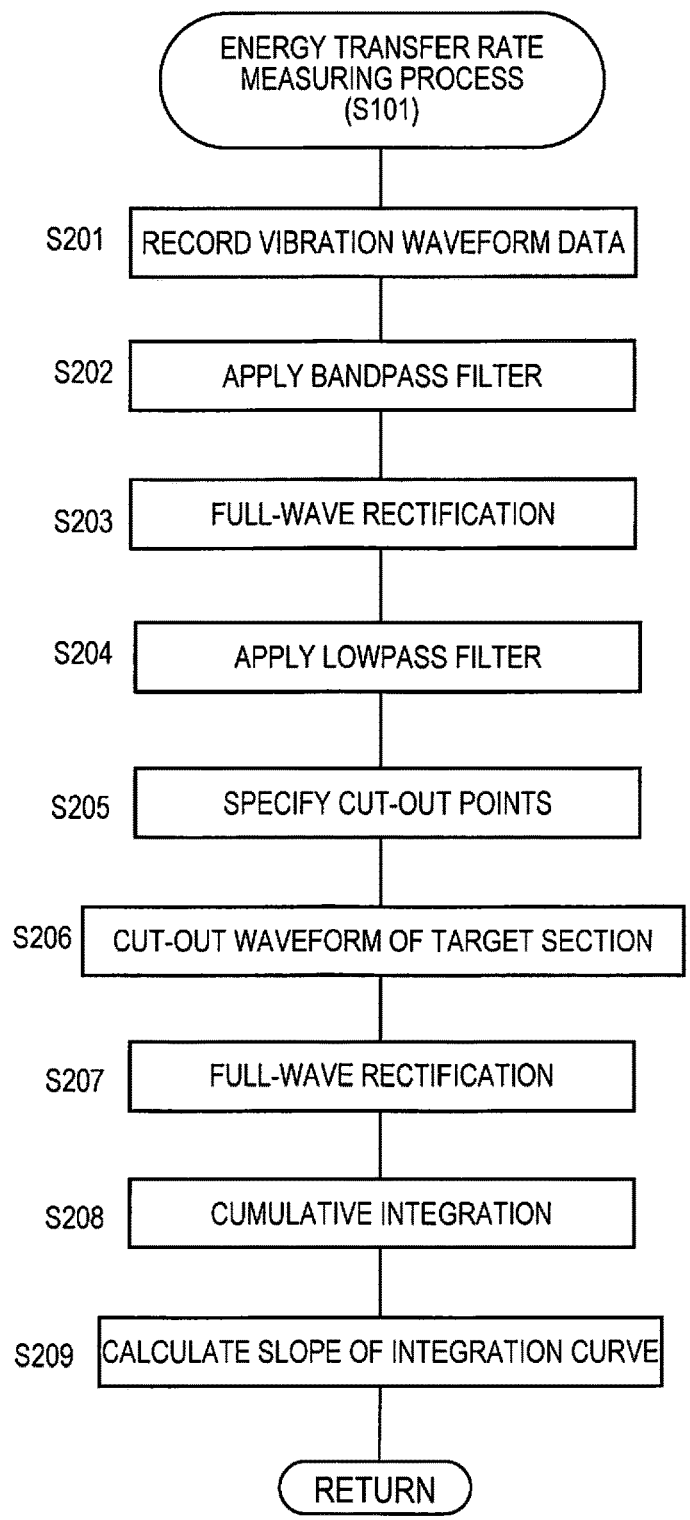
FIG. 4 is a flowchart showing a procedure of the energy transfer rate measuring process shown in step S101 in FIG. 3.

FIG. 4 is a flowchart showing a procedure of the energy transfer rate measuring process shown in step S101 in FIG. 3. FIGS. 5 to 13 are views showing the analysis results of the vibration waveform data of the anvil 220 obtained when processed in accordance with the flowchart shown in FIG. 4. Below, with reference to FIGS. 4 to 13, a description will be given of the energy transfer rate measuring process in detail.

First, the vibration waveform data is recorded (step S201). Specifically, while the ultrasonic bonding apparatus 200 is ultrasonically bonding the plate material W, the vibration amplitude of the anvil 220 is measured by a vibration sensor 110, and the output of the vibration sensor 110 is recorded as the vibration waveform data.

Subsequently, a band pass filter (hereinafter, referred to as "BPF") is applied (step S202). Specifically, the BPF is applied to the vibration waveform data recorded in the process shown in Step S201 to extract data of a predetermined frequency band. The BPF is a FIR (Finite Impulse Response) filter having the vibration frequency of the horn 210 (e.g., 20 kHz) as the center frequency with a constant bandwidth (e.g., ±500 Hz) from the center frequency.

Figure 5:
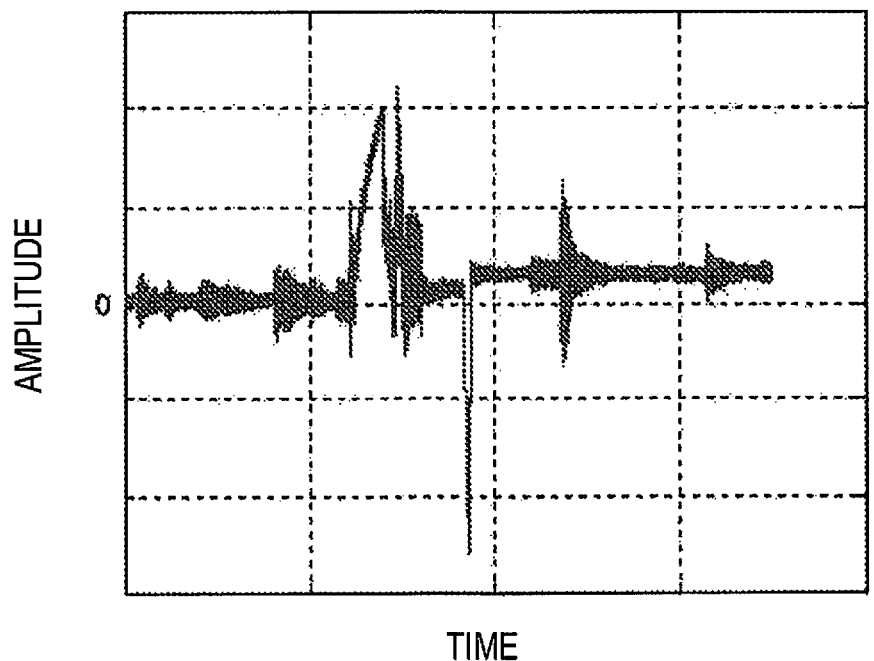
FIG. 5 is a diagram showing an example of vibration waveform data.
Figure 6:
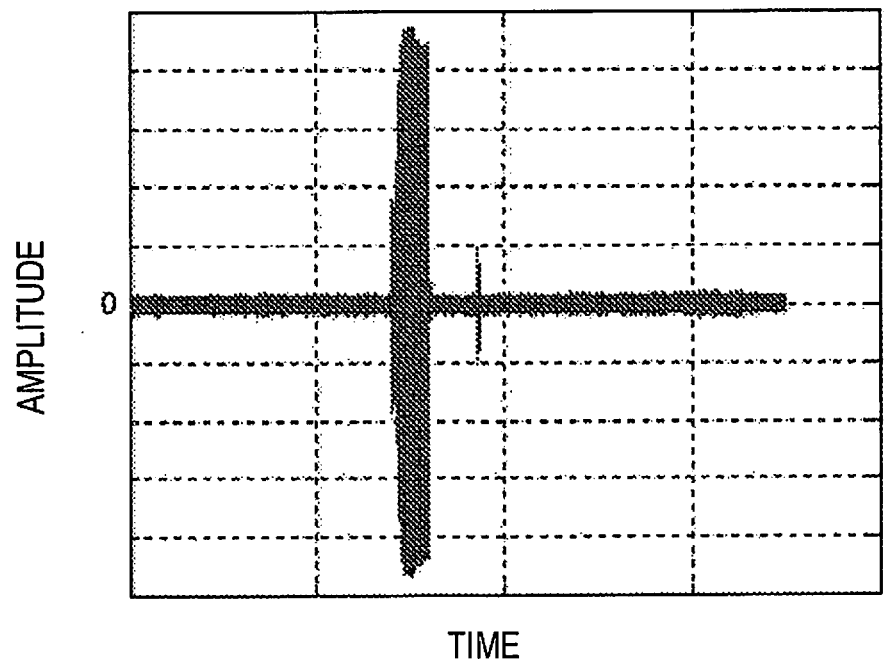
FIG. 6 is a diagram showing vibration waveform data with a bandpass filter applied.

FIG. 5 is a diagram showing an example of the vibration waveform data, FIG. 6 is a diagram showing a vibration waveform data when the BPF is applied. The vertical axis in FIGS. 5 and 6 represents the vibration amplitude of the anvil 220 (output voltage of the vibration sensor 110), while the horizontal axis represents time (number of sampling points).

In the first embodiment, as shown in FIG. 5, the output of the vibration sensor 110 is recorded as the vibration waveform data. The vibration waveform data includes data before the ultrasonic bonding apparatus 200 starts before ultrasonic bonding and data after the ultrasonic bonding apparatus 200 completes ultrasonic bonding. When the recorded vibration waveform data is applied with the BPF, as shown in FIG. 6, such vibration waveform data may be extracted of the center frequency 20 kHz with bandwidth±500 Hz.

Figure 7:
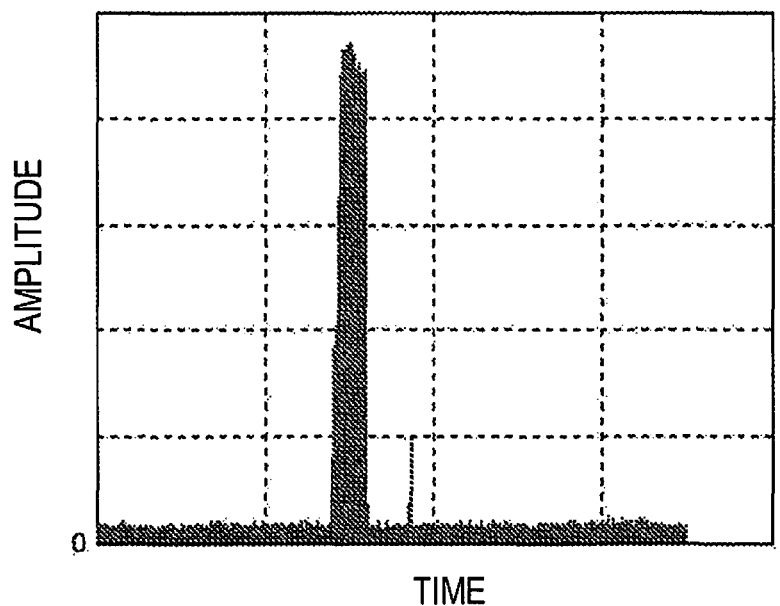
FIG. 7 is a diagram showing vibration waveform data with a full-wave rectification applied.

Subsequently, full-wave rectification is performed (step S203). Specifically, the full-wave rectification is performed on the vibration waveform data after the BPF is applied in the process shown in step S202. When full-wave rectification is performed, as shown in FIG. 7, the amplitude value of the negative side of the vibration waveform data is inverted.

Figure 8:
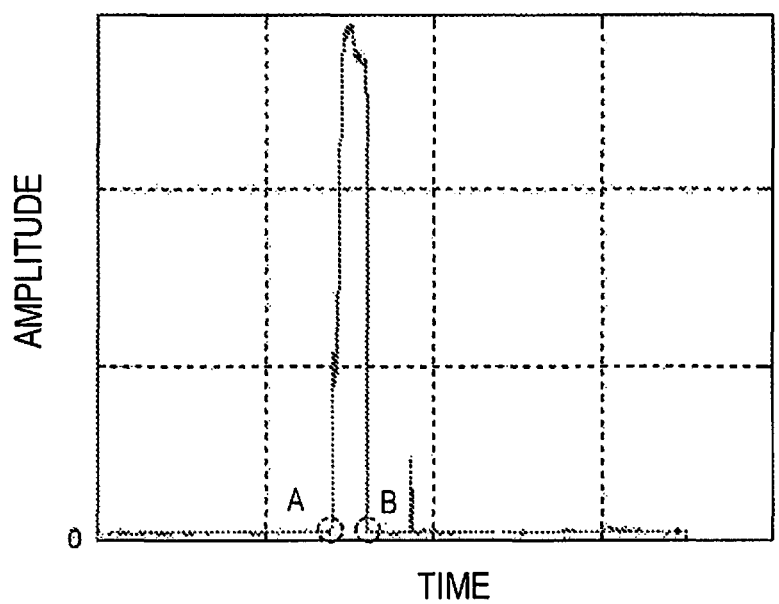
FIG. 8 is a diagram showing vibration waveform data with a low-pass filter applied.

Subsequently, a low-pass filter (hereinafter, referred to as "LPF") is applied (step S204). Specifically, the LPF is applied to the vibration waveform data full-wave on which rectification is performed in the process shown in step S203. When the LPF is applied, as shown in FIG. 8, the envelope of the vibration waveform data is extracted.

Subsequently, a cut out point is specified (step S205). Specifically, based on the vibration waveform data after the LPF is applied in the process shown in step S204, out of the vibration waveform data, the start and end points are respectively specified for cutting out the data of the time while the anvil 220 is vibrating.

Figure 9:
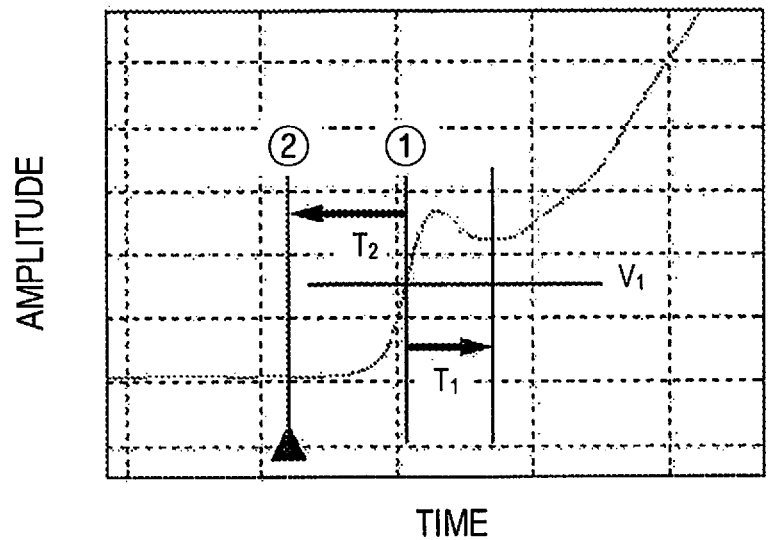
FIG. 9 is a diagram explaining a start point specifying method in a clipping point specifying process.
Figure 10:
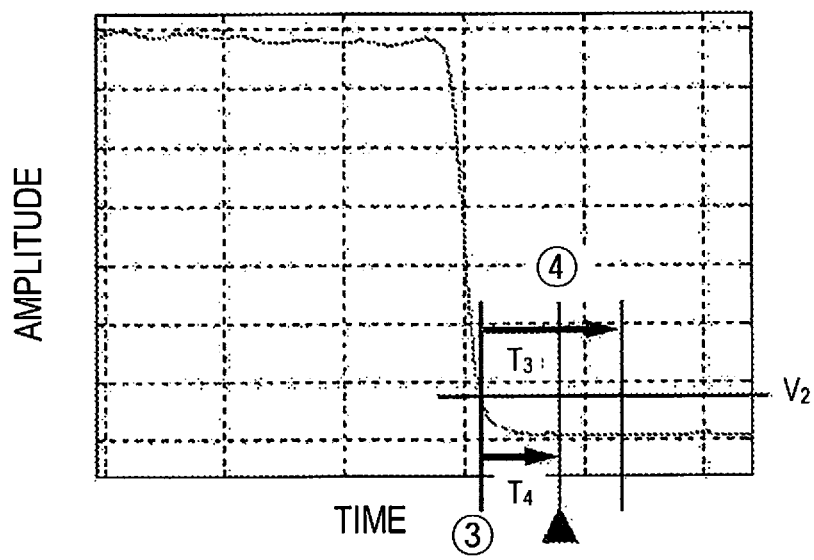
FIG. 10 is a diagram explaining an end point specifying method in a clipping point specifying process.

FIGS. 9 and 10 are diagrams for explaining a cut point specifying process. FIG. 9 is an enlarged view of a portion A surrounded by a broken line in FIG. 8 and FIG. 10 is an enlarged view of a portion B surrounded by another broken line in FIG. 8.

When specifying the start point, as shown in FIG. 9, first, a time in which the amplitude value of vibration waveform data first exceeds a predetermined threshold value $V_1$ (sampling point 1) is recognized. Subsequently, a state in which the amplitude value of the threshold $V_1$ continues to exceed for a predetermined time $T_1$ (a predetermined number of sampling points) is confirmed. When it is confirmed that the state exceeding the threshold $V_1$ continues for the predetermined time period, a time point (sampling point 2) is specified as a start point, which goes back from the sampling point 1 by the predetermined time $T_2$ (a predetermined number of sampling points).

On the other hand, when specifying the end point, as shown in FIG. 10, first, a time point in which the amplitude value of vibration waveform data falls below a predetermined threshold value $V_2$ first (sampling point 3) is recognized. Subsequently, a state in which the amplitude value of the threshold $V_2$ state continues to be below the threshold $V_2$ for a predetermined time $T_3$ is confirmed. When it is confirmed that the state continues to be below the threshold $V_2$ for the predetermined time, a time point (sampling point 4) is specified as the end point, which is advanced from the sampling point 3 by the predetermined time $T_3$.

Figure 11:
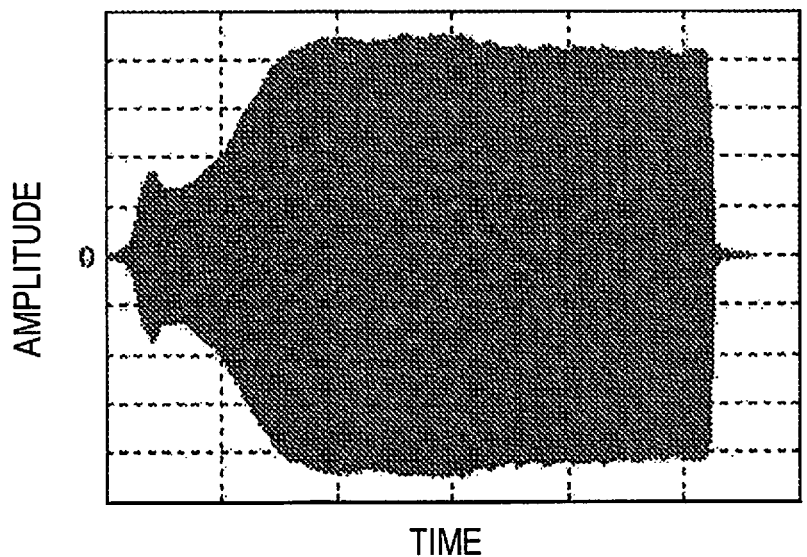
FIG. 11 is a diagram showing vibration waveform data with a waveform of the target section cut out.

Subsequently, the waveform of the target section is cut out (step S206). Specifically, out of the vibration waveform data on which the BPF is applied in the process shown in step S202, time data which is defined and cut out at two cut-out points identified in the process shown in step S205. As a result, as shown in FIG. 11, vibration waveform data is obtained eliminating data that is irrelevant to determine the quality of the bonding state.

Figure 12:
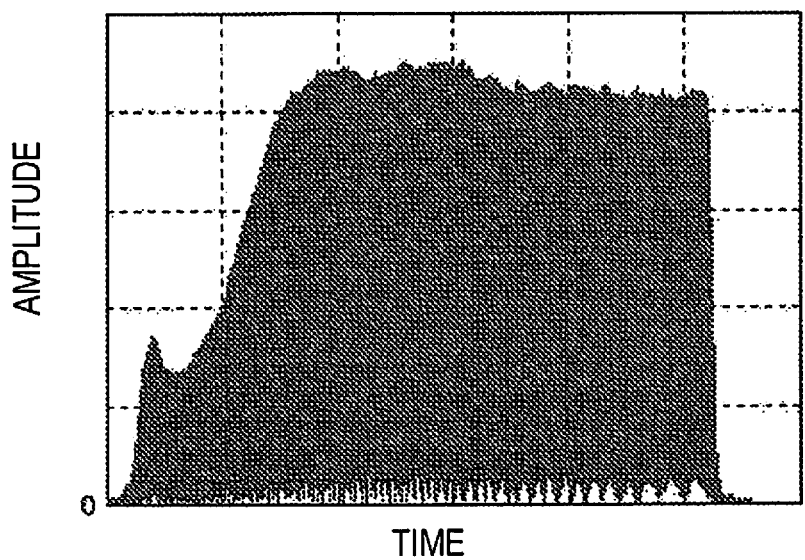
FIG. 12 is a diagram showing vibration waveform data after a full-wave rectification.

Subsequently, full-wave rectification is performed (step S207). Specifically, full-wave rectification is performed on the vibration waveform data cut out in the process shown in step S206. When full-wave rectification is performed, as shown in FIG. 12, the amplitude value of the negative side of the vibration waveform data is inverted.

Subsequently, cumulative integration is performed (step S208). Specifically, the cumulative integral of the vibration waveform data on which the full-wave rectification is applied is obtained in the process shown in step S207. More specifically, the amplitude values at each of the sampling points in the vibration waveform data is accumulated.

Subsequently, the slope of the integration curve is calculated (step S209). Specifically, by dividing the cumulative integral value of the vibration waveform data on which the cumulative integral is performed in the process shown in step S208 by the time extending from the start point of the integration curve to the end point (integration time), the slope of the integral curve of the vibration waveform data is calculated.

Figure 13:
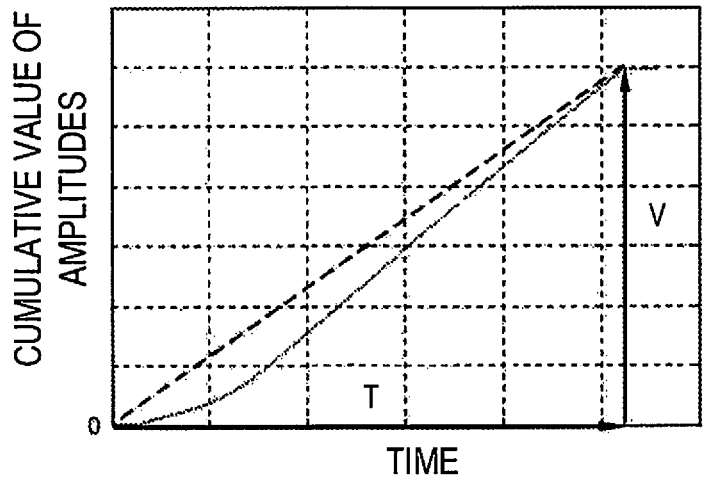
FIG. 13 is a diagram showing a cumulative integral result of the vibration waveform data.

FIG. 13 is a diagram showing the cumulative integral result of the vibration waveform data. In the first embodiment, by dividing the cumulative integral value V of the vibration waveform data by the time T from the start point to the end point of the integration curve, the slope of the integration curve of the vibration waveform data (V/T) is calculated. Note that the cumulative integral value V corresponds to the area value of the vibration waveform data shown in FIG. 11. Further, the area value of the cumulative integral value V and the vibration waveform data correspond to energy transferred to the anvil 220 when the ultrasonic bonding of the plate material W is performed by the ultrasonic bonding apparatus 200. Thus, the integral curve slope (V/T) is equivalent to the energy transfer rate to the anvil 220 per unit time.

Variable Threshold Calculation Process

Figure 14:
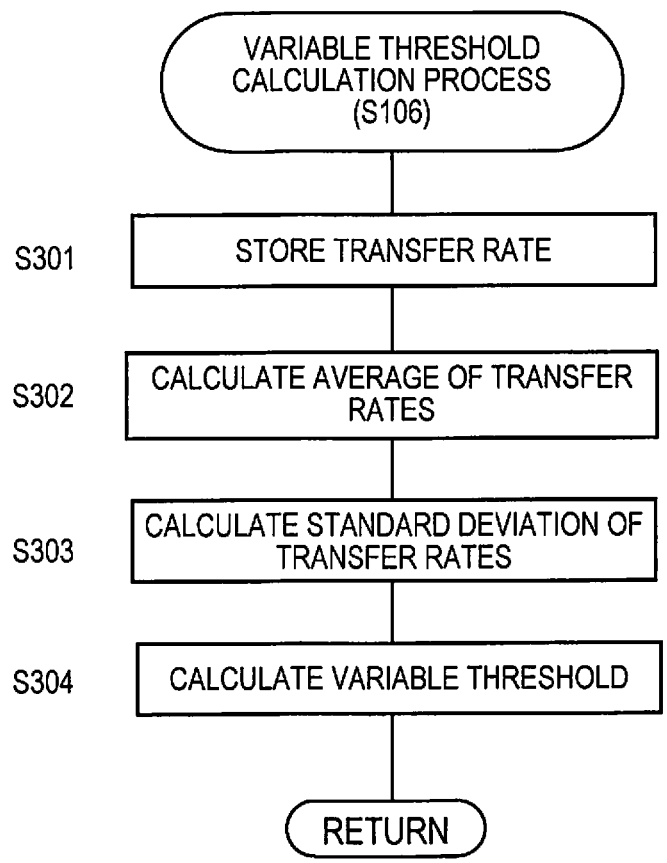
FIG. 14 is a flowchart showing a variable threshold calculation process shown in step S106 in FIG. 3.

FIG. 14 is a flowchart of a variable threshold calculation process shown in step S106 in FIG. 3.

First, the transfer rate is stored (step S301). Specifically, the measured energy transfer rate in the process shown in step S101 in FIG. 3 is stored in the hard disk 124 while allocating an area required for each anvil 220 to be used for ultrasonic bonding.

Subsequently, the average value of the transfer rates is calculated (step S302). Further, the standard deviation of the transfer rates is calculated (step S303). Specifically, based on the stored transfer rate in the process of the step S301 and the other transfer rate already stored in the hard disk 124 for the same anvil 220, the average value of the transfer rates as well as the standard deviation are calculated.

Subsequently, a variable threshold is calculated (step S304). More specifically, the variable threshold is calculated based on the average value calculated in the process of step S302 and the standard deviation calculated in the process of step S303. For example, the variable threshold may be calculated by subtracting four times of the standard deviation from the average value.

As described above, according to the bonding state inspection method pertaining to the first embodiment, by comparing the energy transfer rate to the anvil 220 that is measured each time of the ultrasonic bonding with the magnitude of the variable threshold calculated in the previous ultrasonic bonding, the quality of the bonding state of the plate material W is determined. Thus, even if the measured waveform of the vibration of the anvil 220 is different from the standard waveform, a correct determination can be made. That is, it is possible to determine accurately the quality of the bonding state of the plate material W.

In the bonding state inspection method pertaining to the first embodiment, regardless of the quality of the bonding state of the sheet material W to be ultrasonically bonded, the energy transfer rate with which the bonding state is determined unacceptable is also used to calculate the variable threshold. Note that the present invention is not limited thereto. Thus, without using energy transfer rate when the bonding state is determined unacceptable, the variable threshold may be calculated based on only the energy transfer rate with which the bonding state is determined to be good. For example, in the flowchart of FIG. 3, after the step S105 is performed, without a step S106 being executed, the process may be terminated. Since the variable threshold is calculated based on only the transfer rates with which the bonding is determined to be good, the reliability of the calculated variable threshold will be increased.

Further, in the bonding state inspection method pertaining to the first embodiment, regardless of the bonding number of ultrasonic bonding, using all of the energy transfer rates which are measured each time of the ultrasonic bonding, the variable threshold is calculated. Note that the present invention is not limited thereto. Thus, by using a predetermined number of energy transfer rates which are measured immediately before, the variable threshold may be calculated. For example, in the flowchart of FIG. 14, in the process shown in step S301, the energy transfer rate up to a predetermined number may be stored in FIFO (First In, First Out) method. Since the number of data used to calculate the variable threshold will be reduced relatively small, the processing load for calculating the variable threshold (process time and memory use) is reduced.

Further, in the bonding state inspection method pertaining to the first embodiment, regardless of the bonding number of ultrasonic bonding, the variable threshold is calculated each time of the ultrasonic bonding. When the transfer rate does not exceed the fixed threshold value, it is determined whether or not the variable threshold that has been calculated in a previous ultrasonic bonding is exceeded. However, the present invention is not limited thereto. When the bonding number does not reach a predetermined number of times, only the transfer rate is stored, and the variable threshold may be calculated after the bonding number has reached the predetermined number of times. For example, in the flowchart of FIG. 14, when the number of stored transfer rates in the process shown in step S301 does not reach the predetermined number, the procedure may return without executing the process shown in steps S302~S304. Since it is not necessary to calculate the variable threshold in a stage with the small number of bonding, processing load for calculating the variable threshold (processing time and memory use) is reduced.

Second Embodiment

In the first embodiment described above, when the energy transfer rate to the anvil 220 does not exceed the fixed threshold, by comparing the energy transfer rate and the variable threshold, the quality of the bonding state is determined. In a second embodiment, the bonding number of ultrasonic bonding is counted. When the count does not exceed a predetermined number of times, the transfer rate is compared to a fixed threshold, whereas, when the bonding number exceeds the predetermined number, the transmission rate is compared to the variable threshold to determine the quality of the bonding state.

The inspection apparatus to which the bonding state inspection method pertaining to the second embodiment is applied may be similar to the inspection apparatus 100 to which the bonding state inspection method pertaining to the first embodiment. Below, a description will be given in detail of the bonding state inspection method pertaining to the second embodiment.

Figure 15:
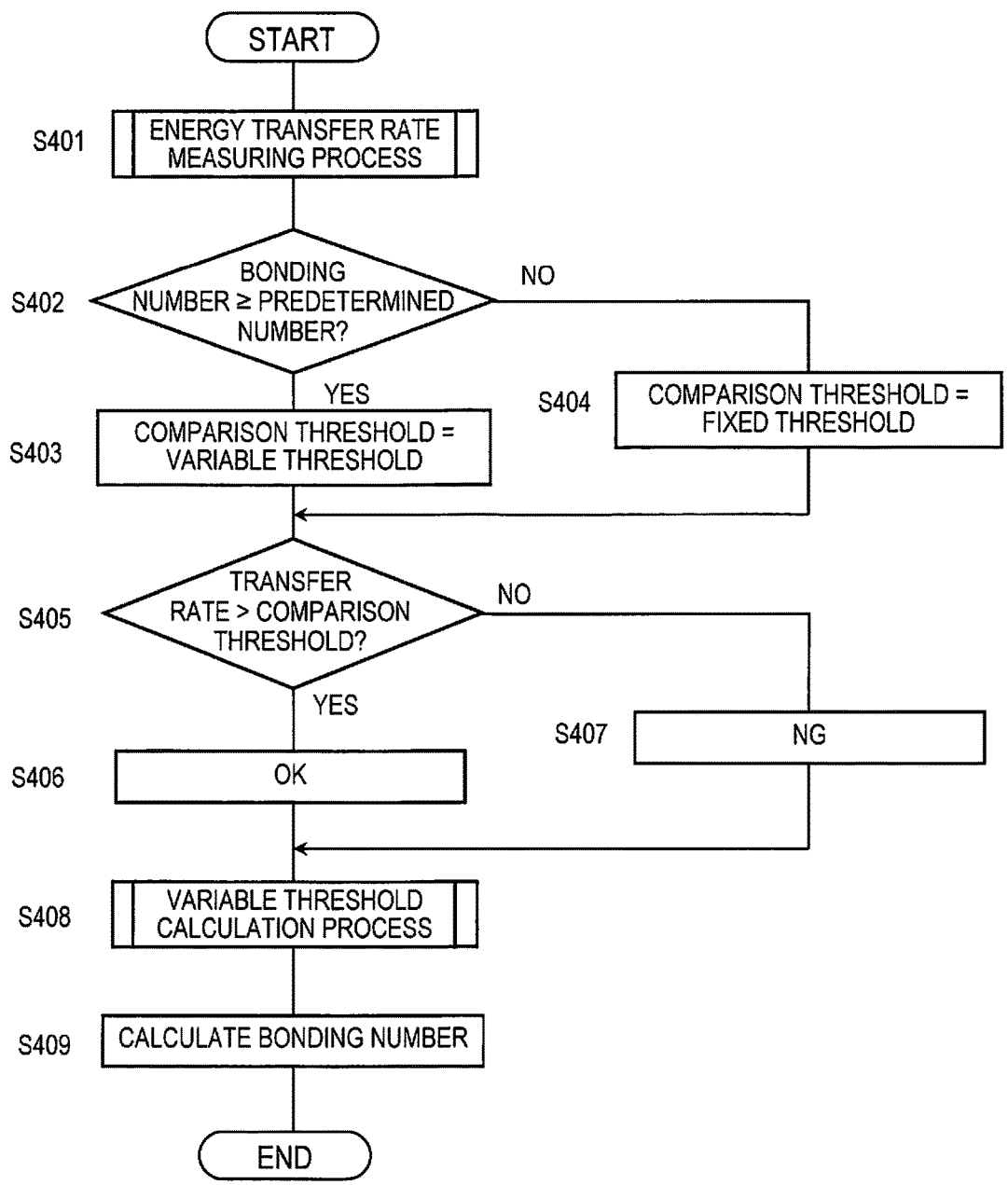
FIG. 15 is a flowchart showing a bonding state inspection process pertaining to a second embodiment.

FIG. 15 is a flowchart showing a bonding state inspection process pertaining to the second embodiment.

The process shown in steps S401, S408 of the second embodiment is the same as the process shown in steps S101, S106 of the first embodiment. Accordingly, in the second embodiment, a detailed description of the same process as the first embodiment will be omitted.

First, an energy transfer rate measuring process is executed (step S401). Subsequently, it is determined whether or not the bonding number is a predetermined number of times or more (step S402). More specifically, it is determined whether or not the bonding number of ultrasonic bonding using the same anvil 220 is equal to the predetermined number of times or more. When the bonding number is equal to or larger than the predetermined number of times (step S402: YES), the variable threshold is substituted for a comparison threshold (step S403). On the other hand, when the bonding number is less than the predetermined number of times (step S402: NO), a fixed threshold is substituted for the comparison threshold value (step S404). Here, the variable threshold as well as the fixed threshold are defined similarly as in the first embodiment.

Subsequently, it is determined whether or not the energy transfer rate calculated in the process shown in step S401 exceeds the comparison threshold value (step S405). When the transfer rate does not exceed the comparison threshold value (step S405: NO), the bonding state is determined to be unacceptable or poor (step S407). On the other hand, when the transfer rate exceeds the comparison threshold value (step S405: YES), the bonding state is determined to be satisfactory or good (step S406).

Subsequently, after a variable threshold calculation process (step S408) is performed, the bonding number is calculated (step S409). Specifically, it is possible to count up the number of times in which the ultrasonic bonding using the same anvil 220 so as to calculate a count value as the bonding number. Alternatively, only when the bonding state is determined to be good, the bonding number may be counted. Note that the present invention is not limited thereto. The bonding number of times can be calculated directly from the number of the energy transfer rates for each anvil 220 stored in the hard disk 124. Note that, when the anvil 220 is exchanged, the bonding number of times is reset to an initial value such as zero (0).

As described above, in the bonding state inspection method, the same effects as the first embodiment may be obtained.

Further, according to the bonding state inspection method pertaining to the second embodiment, in accordance with the bonding number of ultrasonic bonding, either the fixed threshold value or the variable threshold is selected for comparison in magnitude with the energy transfer rate to the anvil. Therefore, compared to a case in which the energy transfer rate is compared to both the fixed threshold and the variable threshold as in the first embodiment, processing load of the analysis device 120 is reduced.

Below, with reference to FIGS. 16 to 18, a description will be given in detail of operational effects of the bonding state inspection method according to the present invention.

Figure 16:
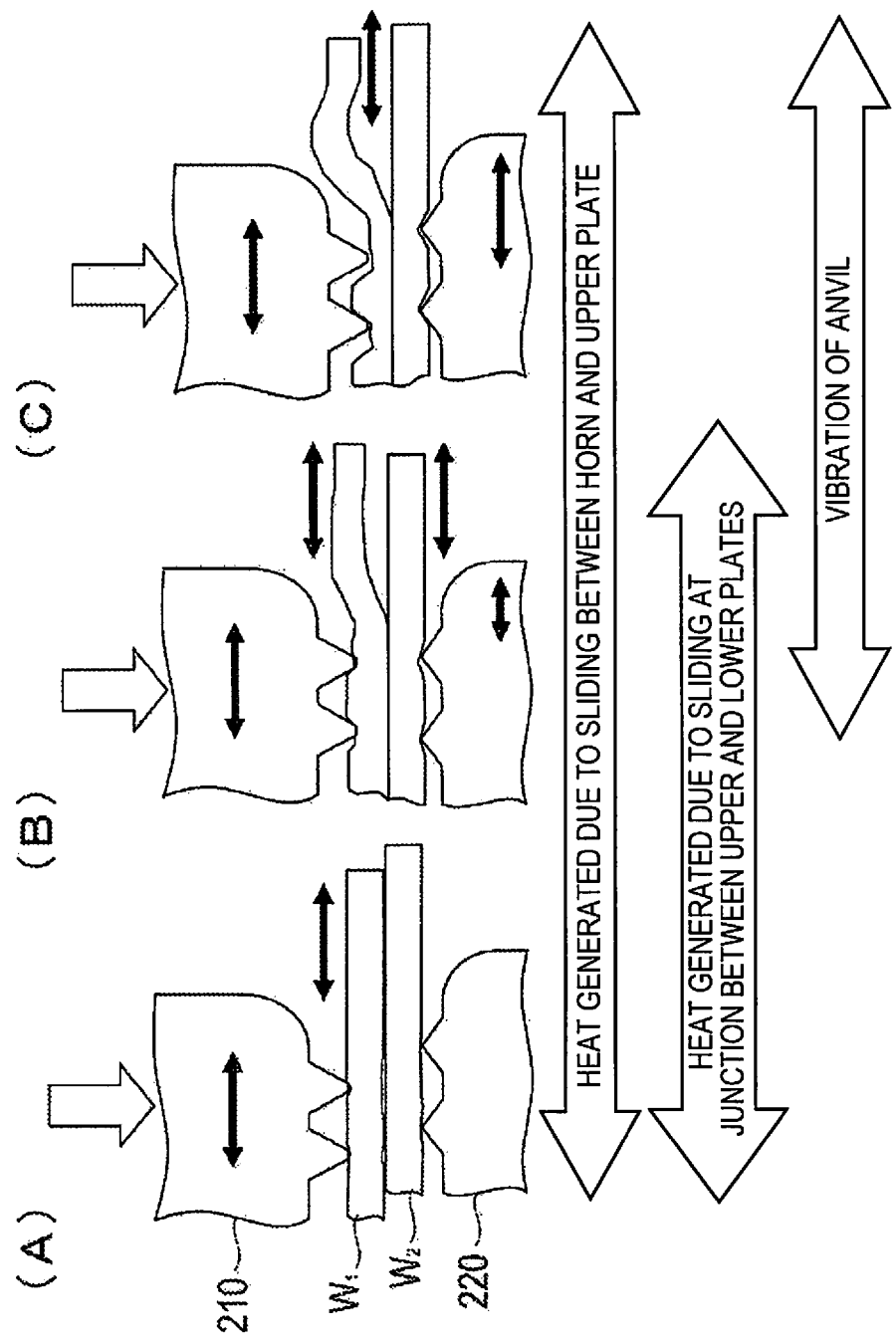
FIG. 16 is a diagram showing the behavior of the anvil at the time of ultrasonic bonding.

FIG. 16 is a diagram illustrating the behavior of the anvil 220 during ultrasonic bonding. With respect to two plate materials $W_1$ and $W_2$, the plate material $W_2$ is placed on the anvil 220, while the plate material $W_1$ is placed on top of the plate material $W_2$. During ultrasonic bonding, the horn 210 continues to vibrate while pressing against the plate material $W_1$ up to a predetermined time (tact time) so as to impart the own vibration to the plate material $W_1$. Note that the ultrasonic bonding apparatus 200 applies power to the horn 210 so as to maintain the amplitude and pressure of the horn 210 at constant.

As shown in FIG. 16(A), immediately after the start of the ultrasonic bonding, the two plate materials $W_1$ and $W_2$ are not bonded so that the vibration of the horn 210 is transmitted only to the upper plate material $W_1$. Thus, the anvil 220 does not vibrate, and heat will be generated due to sliding between the horn 210 and the plate material $W_1$. Also, heat will be generated due to sliding between the plate materials $W_1$ and $W_2$.

As shown in step (B) of FIG. 16, when the plate material $W_1$ and the plate material $W_2$ start to be bonded, the vibration of the horn 210 is transmitted to the anvil 220 to start the anvil 220 vibrating.

As shown in step (C) FIG. 16, bonding between the plate material $W_1$ and the plate material $W_2$ proceeds, the plate material $W_1$ and the plate material $W_2$ will not slide to each other, and heat generation due to the sliding between the plate material $W_1$ and the plate material $W_2$ is eliminated. On the other hand, the anvil 220 vibrates larger than in the case shown in step B of FIG. 16.

As described above, in the ultrasonic bonding, in accordance with the bonding state of the bonding interface or junction between the two plate materials $W_1$ and $W_2$, the energy transferred from the horn 210 to the anvil 220 through the plate materials $W_1$ and $W_2$ in the tact time is changed. Also, due to the influence of deformation or dirt of the plate materials $W_1$ and $W_2$, even when the vibration amplitude of the horn 210 is measured, the correlation with the bonding state of the bonding interface of the plate material $W_1$ and $W_2$ is not acquired so that the bonding state would not be determined correctly.

Further, in the ultrasonic bonding, the anvil 220 is pressurized and vibrated through the two plate materials $W_1$ and $W_2$. Therefore, each time ultrasonic bonding is performed, the tip of the anvil 220 of grid-like projections, on which the plate material $W_2$ is placed, is worn, and the life of the anvil 220 will be shortened. When the bonding number of ultrasonic bonding continues to increase, wear will be serious, and the anvil 220 and the plate material $W_2$ slide to each other. In the ultrasonic bonding, sliding between the anvil 220 and the sheet material $W_2$ will reduce the energy transferred from the horn 210 to the anvil 220. Accordingly, the plate materials $W_1$ and $W_2$ even show a good bonding state at the bonding interface, the energy transferred to the anvil 220 within the tact time changes over time depending on the lifetime of the anvil 220. Therefore, even by measuring the vibration amplitude of the anvil 220, a case arises in which the bonding state cannot be determined properly because the change of the vibration waveform is not ascertained to be attributable to the bonding state at the bonding interface of the plate materials $W_1$ and $W_2$ or attributable to the life of the anvil 220.

On the other hand, in the bonding state inspection method according to the present invention, by measuring the vibration amplitude of the anvil 220, the energy transfer rate to the anvil 220 is measured, which indicates actual condition or requirement for ultrasonic bonding. In addition, by comparing the energy transfer rate with the magnitude of the variable threshold calculated in the previous ultrasonic bonding, the quality of the bonding state of the sheet material W is determined. Since the variable threshold is calculated using the energy transfer rate to the anvil 220 as measured each time of the ultrasonic bonding, the influence of the life of the anvil 220 is reflected in the energy transfer rate. Therefore, the change due to the influence of the lifetime of the anvil 220 is eliminated from the energy transfer rate representing the true requirement of the ultrasonic bonding, the quality of the bonding state can be determined accurately.

In addition, in the bonding state inspection method according to the present invention, the vibration amplitude of the anvil 220 is measured by the vibration sensor 110 of the non-contact type. Thus, without affecting the vibration state by the self-weight of the sensor as in the case of a vibration sensor of contact type, the behavior of the anvil 220 may be measured correctly.

Figure 17:
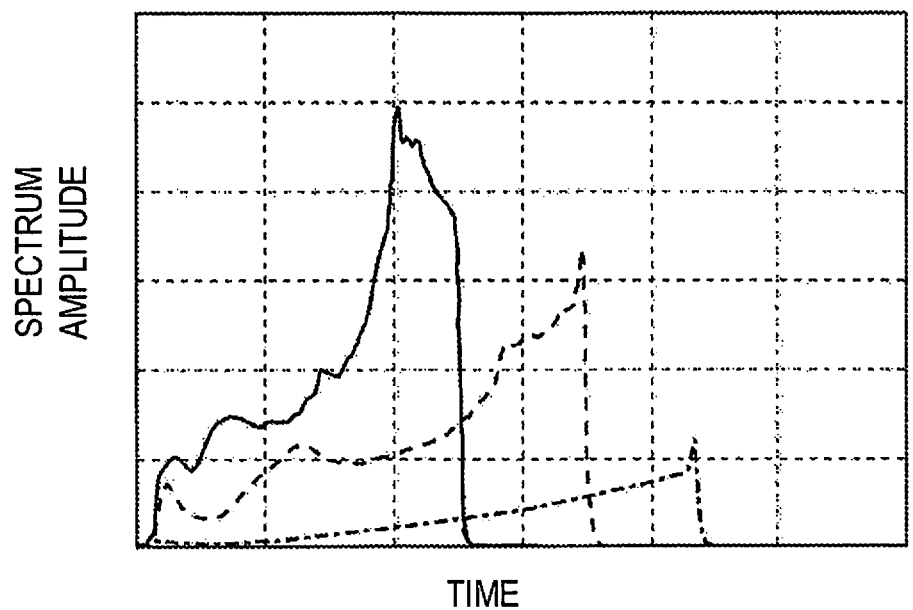
FIG. 17 is a diagram explaining the effect of the bonding state inspection method.

FIG. 17 is a diagram for explaining an effect of the bonding state inspection method according to the present invention. The vibration waveforms which are shown by solid line and broken line in FIG. 17 represent vibration waveforms of good products which are determined to be good in bonding state (bonding strength) in a tensile test. On the other hand, the vibration waveform shown by one-dot chain line in FIG. 17 represents a vibration waveform of defective product which is determined poor in the bonding state in a tensile test.

As shown in FIG. 17, in the defective product, compared to the good products, energy is less transmitted to the anvil 220. On the other hand, the comparison in the vibration waveforms between the good products in solid line and in broken line confirms a difference in the waveform. In the conventional monitoring method of comparing the measured waveform with the standard waveform, product of the vibration waveform shown in broken line, is determined to be defective.

However, in the bonding state inspection method according to the present invention, determination on the acceptability of the bonded state is made based on energy transfer rate to the anvil. Thus, even those products which would be determined to be defective when attention is paid to the measured waveform would be determined as good and non-defective product.

Figure 18:
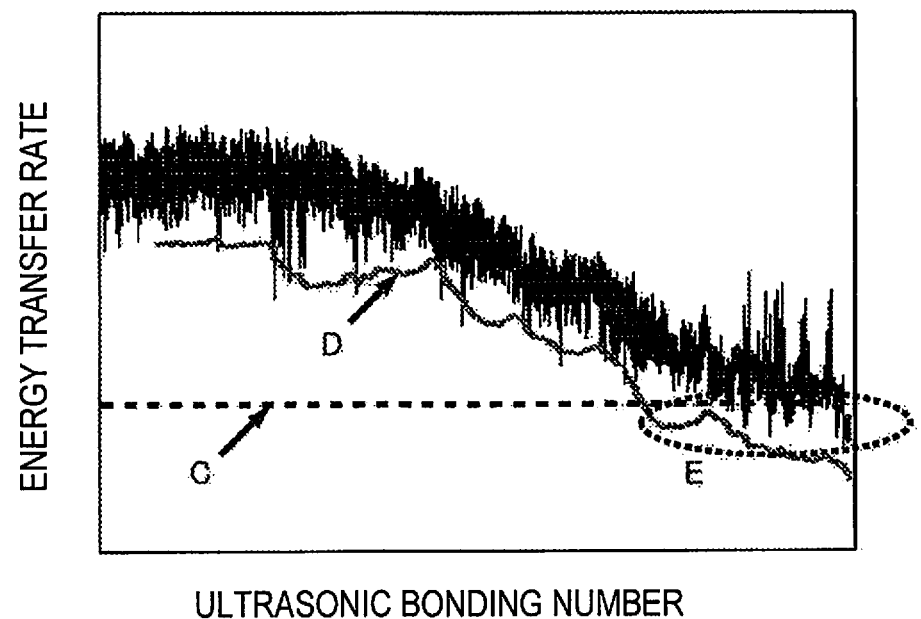
FIG. 18 is a diagram explaining the effect of the life of the anvil with respect to the energy transfer rate to the anvil.

FIG. 18 is a diagram for explaining the influence of the life of the anvil with respect to the energy transfer rate to the anvil 220. In FIG. 18, the horizontal axis represents the ultrasonic bonding number (welding spot points) and the vertical axis represents the energy transfer rate to the anvil 220 that is measured each time of the ultrasonic bonding. Note that the broken line C indicates a fixed threshold obtained statistically in advance, and the solid line D indicates the variable threshold calculated using the energy transfer rate to the anvil each time of the ultrasonic bonding. Furthermore, the region E is a region where energy transfer rate which does not exceed the fixed threshold value, yet exceeding the variable threshold.

As shown in FIG. 18, as the ultrasonic bonding number is increased, the energy transfer rate to the anvil 220 decreases with time. As described above, this is believed to occur due to wear of the anvil 220 that is used in ultrasonic bonding, because the anvil 220 and the plate material W slide to each other so that the energy transferred to the anvil 220 in the tact time. That is, as the ultrasonic bonding number is increased, even in products in which the bonding state is good, the energy transfer rate to the anvil 220, as measured by the analysis device 120, decreases with time.

Thus, as the bonding number of ultrasonic bonding approaches the life expectancy of the anvil 220, as shown in area E, the energy transfer rate is often lower than the fixed threshold. Accordingly, also in the area E, in the method for determining the quality of the bonding state by comparing the energy transfer rate to the anvil 220 and the fixed threshold value, the bonding state of the product is often determined to be defective so that defective products will be excessively detected. In this case, in the manufacturing site, considering the yield, even if the original life of the anvil 220 is not yet over, the anvil is forced to be replaced. Since the anvil 220 is not effectively used to the original lifetime, the situation would lead to increase in production cost.

However, in the bonding state inspection method according to the present invention, in order to determine the quality of the bonding state, the energy transfer rate to the anvil is compared with a variable threshold. Thus, even in the area E, it is possible to prevent over-detection of the defective products so that the anvil 220 can continue to be used until the original lifetime.

Thus, in the bonding state inspection method according to the present invention, the determination accuracy in the bonding state of plate materials may be improved. As a result, the products that are determined to be defective or poor will be reduced so as to improve the yield of the product. The manufacturing cost is also reduced.

As described above, the present embodiment described above has the following effects.

(a) In a bonding state inspection method according to the present invention, by comparing the energy transfer rate to the anvil with the magnitude of a variable threshold calculated in the previous ultrasonic bonding, the quality of the bonding state of the plate material is determined. Thus, correct determination may be made even when the measured waveform of the vibration amplitude of the anvil is different from the standard waveform. That is, the quality of the bonding state of the plate materials can be determined accurately.

(b) In the bonding state inspection method according to the present invention, when the energy transfer rate does not exceed the variable threshold, the bonding state of the plate materials is determined to be poor. Accordingly, the influence of the life of the anvil with respect to the energy transfer rate is removed. Even when the anvil is used close to the life, the quality of the bonding state of the plate materials may be determined correctly.

(c) In the bonding state inspection method according to the present invention, the variable threshold is calculated based on an average of energy transfer rates measured each time of the ultrasonic bonding and a standard deviation thereof. Therefore, the influence of the life of the anvil with respect to the energy transfer rate can be reflected accurately to calculate the variable threshold.

(d) In the bonding state inspection method according to the present invention, among the energy transfer rates to the anvil, those transfer rates determined with good bonding state are used to calculate the variable threshold. In this case, enhanced reliability of the calculated variable threshold may be achieved.

(e) In the bonding state inspection method according to the present invention, among the energy transfer rates to the anvil, a predetermined number of energy transfer rates which are measured immediately before is used to calculate the variable threshold. Accordingly, it is possible to reduce the processing load for calculating the variable threshold.

(f) In the bonding state inspection method according to the present invention, depending on the bonding number of ultrasonic bonding, either a fixed threshold or a variable threshold for energy transfer rate is selected for comparison in magnitude with the energy transfer rate to the anvil. Therefore, compared to a case in which the energy transfer rate is compared to both the fixed threshold and the variable threshold, processing load on the analysis device may be reduced.

(g) That bonding number of ultrasonic bonding may be specific to corresponding to that of ultrasonic bonding in which bonding state is determined to be good in the plate materials. Therefore, it is possible to easily calculate the variable threshold with the energy transfer rates in which the bonding state is determined to be good.

(h) In the bonding state inspection method according to the present invention, by dividing the integration value of the vibration waveform data by the integration time to obtain a value for comparison with the variable threshold, it is determined whether or not the bonding state of the plate materials is good.

Therefore, variations in the bonding time may be absorbed, and stability of the determination is improved.

(i) In the bonding state inspection method according to the present invention, among the vibration waveform data, such data is to be cut out or extracted during a time in which the anvil is vibrating to integrate the extracted data. Accordingly, the data amount is reduced, thereby enabling determination of the quality of the bonding state in a short time.

(j) In the bonding state inspection method according to the present invention, a BPF with a frequency band determined by the vibration frequency of the horn is applied to extract data from the vibration waveform data. Accordingly, it is possible to remove the disturbance (noise) included in the vibration waveform data.

(k) In the bonding state inspection method according to the present invention, the center frequency of the BPF corresponds to the vibration frequency of the horn. Accordingly, only the energy which is transferred from the horn may be selectively extracted.

As described above, a description is given of the preferred embodiments of according to the present invention. These are examples for explaining the present invention. Needless to say, in the present invention, addition, deformation, and omission may be made appropriately within the scope of the technical idea as obvious to those skilled in the art.

DESCRIPTION OF REFERENCE NUMERALS 100 inspection apparatus,
110 vibration sensor,
120 analysis device,
121 CPU,
122 ROM,
123 RAM,
124 hard disk,
125 display,
126 input unit,
127 interface,
200 ultrasonic bonding apparatus,
210 horn,
220 anvil.

The invention claimed is:

1. A bonding state inspection method comprising:
measuring an energy transfer rate to an anvil each of a plurality of times a vibrating horn is pressed against a plurality of superimposed plate materials that are placed on the anvil and an ultrasonic bonding is performed;
calculating a variable threshold of the energy transfer rate using the energy transfer rate which is measured each of the plurality of times the ultrasonic bonding is performed; and
determining a quality of a bonding state of the plate materials by comparing the energy transfer rate which is measured one of the plurality of times the ultrasonic bonding is performed with the variable threshold which has been calculated in a previous one of the plurality of times the ultrasonic bonding is performed,
the energy transfer rate being a slope of an integral curve of vibration waveform data of the anvil, and
the variable threshold being calculated based on at least one of an average value of the energy transfer rates measured each of the plurality of times the ultrasonic bonding is performed and a standard deviation thereof.

2. The bonding state inspection method as claimed in claim 1, wherein
among the energy transfer rates to the anvil that are measured each of the plurality of times the ultrasonic bonding is performed, a predetermined number of energy transfer rates which are measured immediately before the one of the plurality of times is used to calculate the variable threshold.

3. The bonding state inspection method as claimed in claim 1, wherein
the measuring the energy transfer rate further comprises:
measuring a vibration amplitude of the anvil using a vibration sensor, and
integrating the vibration waveform data obtained by measuring the vibration amplitude of the anvil,
wherein the determining comprises comparing the variable threshold with a value obtained by dividing an integrated value of the vibration waveform data by an integral time.

4. The bonding state inspection method as claimed in claim 1, wherein
the measuring the energy transfer rate comprises applying a band pass filter with a frequency band determined by a vibration frequency of the vibrating horn is applied to extract data of the frequency band from a vibration data.

5. The bonding state inspection method as claimed in claim 4, wherein
a center frequency of the band pass filter corresponds to the vibration frequency of the vibrating horn.

6. The bonding state inspection method as claimed in claim 1, further comprising
counting to count a bonding number of the ultrasonic bonding, in which in the determining the quality of the bonded state of the plate materials, when the bonding number is less than a predetermined number of times, by comparing the energy transfer rate measured with a predetermined fixed threshold, the quality of the bonding state of the plate materials is determined, and when the bonding number is equal to the predetermined number of times or more, by comparing the energy transfer rate measured with the variable threshold calculated in the previous ultrasonic bonding, the quality of the bonding state of the plate materials is determined.

7. The bonding state inspection method as claimed in claim 6, wherein
during the counting, the bonding number of the ultrasonic bonding is counted, in which the quality of the bonding state is determined to be good in the plate materials.

8. The bonding state inspection method as claimed in claim 7, wherein
the measuring further comprises a cut-out step in which data during a time in which the anvil is vibrating is cut out, and, in the integration step, the data that was cut out in the cut-out step is integrated.

9. The bonding state inspection method as claimed in claim 1, wherein
the quality of the bonding state of the plate materials is determined to be poor when the energy transfer rate measured the one of the plurality of times the ultrasonic bonding is performed does not exceed the variable threshold calculated in a previous one of the plurality of times the ultrasonic bonding is performed.

10. The bonding state inspection method as claimed in claim 9, wherein
among the energy transfer rates to the anvil that are measured each of the plurality of times the ultrasonic bonding is performed, those determined to correspond to a good bonding state are used to calculate the variable threshold.

11. The bonding state inspection method as claimed in claim 9, wherein
among the energy transfer rates to the anvil that are measured each of the plurality of times the ultrasonic bonding is performed, a predetermined number of energy transfer rates which are measured immediately before the one of the plurality of times is used to calculate the variable threshold.

12. The bonding state inspection method as claimed in claim 9, further comprising counting a bonding number of the ultrasonic bonding, in which in the determining the quality of the bonded state of the plate materials, when the bonding number is less than a predetermined number of times, by comparing the energy transfer rate measured with a predetermined fixed threshold, the quality of the bonding state of the plate materials is determined, and when the bonding number is equal to the predetermined number of times or more, by comparing the energy transfer rate measured with the variable threshold calculated in the previous ultrasonic bonding, the quality of the bonding state of the plate materials is determined.

13. The bonding state inspection method as claimed in claim 1, wherein among the energy transfer rates to the anvil that are measured each of the plurality of times the ultrasonic bonding is performed, those determined to correspond to a good bonding state are used to calculate the variable threshold.

14. The bonding state inspection method as claimed in claim 13, wherein among the energy transfer rates to the anvil that are measured each of the plurality of times the ultrasonic bonding is performed, a predetermined number of energy transfer rates which are measured immediately before the one of the plurality of times is used to calculate the variable threshold.

15. The bonding state inspection method as claimed in claim 13, further comprising counting a bonding number of the ultrasonic bonding, in which in the determining the quality of the bonded state of the plate materials, when the bonding number is less than a predetermined number of times, by comparing the energy transfer rate measured with a predetermined fixed threshold, the quality of the bonding state of the plate materials is determined, and when the bonding number is equal to the predetermined number of times or more, by comparing the energy transfer rate measured with the variable threshold calculated in the previous ultrasonic bonding, the quality of the bonding state of the plate materials is determined.

* * * * *